(12) United States Patent
Ditto

(10) Patent No.: US 9,015,056 B2
(45) Date of Patent: Apr. 21, 2015

(54) PRESCRIPTION REFILL REMINDER SYSTEM AND METHOD

(75) Inventor: Steven C. Ditto, Austin, TX (US)

(73) Assignee: Hewlett-Packard Development Company, L. P., Houston, TX (US)

( * ) Notice: Subject to any disclaimer, the term of this patent is extended or adjusted under 35 U.S.C. 154(b) by 2159 days.

(21) Appl. No.: 12/012,836

(22) Filed: Feb. 6, 2008

(65) Prior Publication Data

US 2009/0198510 A1 Aug. 6, 2009

(51) Int. Cl.
*G06Q 50/22* (2012.01)
*G06Q 10/10* (2012.01)
*G06Q 30/02* (2012.01)

(52) U.S. Cl.
CPC .............. *G06Q 50/22* (2013.01); *G06Q 10/109* (2013.01); *G06Q 30/02* (2013.01)

(58) Field of Classification Search
CPC ...................................................... G06Q 50/22
USPC ............................................................ 705/2
See application file for complete search history.

(56) References Cited

U.S. PATENT DOCUMENTS

| | | | | |
|---|---|---|---|---|
| 5,845,255 | A * | 12/1998 | Mayaud | 705/3 |
| 7,711,583 | B2 * | 5/2010 | Epstein et al. | 705/3 |
| 7,734,483 | B1 * | 6/2010 | Smith et al. | 705/3 |
| 2005/0187821 | A1 * | 8/2005 | Lapsker | 705/14 |
| 2006/0161294 | A1 | 7/2006 | DiMaggio | |
| 2006/0161298 | A1 | 7/2006 | DiMaggio | |
| 2006/0247968 | A1 * | 11/2006 | Kadry | 705/14 |
| 2006/0287882 | A1 | 12/2006 | Hansel et al. | |
| 2009/0043609 | A1 * | 2/2009 | Nadas et al. | 705/3 |

* cited by examiner

*Primary Examiner* — Michael Fuelling
(74) *Attorney, Agent, or Firm* — Hewlett-Packard Patent Department

(57) ABSTRACT

A system and method for subscriber reminders. The method includes receiving, from a plurality of customers, prescription refill data. The method also includes processing the prescription refill data according to business rules. The method also includes sending, to a subscriber, a prescription refill reminder according to the prescription refill data and the business rules. The method also includes sending, to the subscriber, advertising data corresponding to the prescription refill reminder.

7 Claims, 4 Drawing Sheets

PRESCRIPTION REFILL REMINDER SYSTEM AND METHOD

TECHNICAL FIELD

The present disclosure is directed, in general, to systems and methods for prescription refill reminders.

BACKGROUND OF THE DISCLOSURE

Many prescription pharmaceuticals and other items, healthcare or otherwise, can only be purchased or ordered on a periodic basis, and must be repurchased or reordered for a new supply when the current purchase is exhausted. In many cases, particularly where the remaining quantity of a good or substance can't easily be determined, a user may wait until the current supply is exhausted before placing an order for a refill.

SUMMARY OF THE DISCLOSURE

According to various disclosed embodiment, there is a system and method for subscriber reminders. The method includes receiving, from a plurality of customers, prescription refill data. The method also includes processing the prescription refill data according to business rules. The method also includes sending, to a subscriber, a prescription refill reminder according to the prescription refill data and the business rules. The method also includes sending, to the subscriber, advertising and informational data corresponding to the prescription refill reminder.

The foregoing has outlined rather broadly the features and technical advantages of the present disclosure so that those skilled in the art may better understand the detailed description that follows. Additional features and advantages of the disclosure will be described hereinafter that form the subject of the claims. Those skilled in the art will appreciate that they may readily use the conception and the specific embodiment disclosed as a basis for modifying or designing other structures for carrying out the same purposes of the present disclosure. Those skilled in the art will also realize that such equivalent constructions do not depart from the spirit and scope of the disclosure in its broadest form.

Before undertaking the DETAILED DESCRIPTION below, it may be advantageous to set forth definitions of certain words or phrases used throughout this patent document: the terms "include" and "comprise," as well as derivatives thereof, mean inclusion without limitation; the term "or" is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, whether such a device is implemented in hardware, firmware, software or some combination of at least two of the same. It should be noted that the functionality associated with any particular controller may be centralized or distributed, whether locally or remotely. Definitions for certain words and phrases are provided throughout this patent document, and those of ordinary skill in the art will understand that such definitions apply in many, if not most, instances to prior as well as future uses of such defined words and phrases.

BRIEF DESCRIPTION OF THE DRAWINGS

For a more complete understanding of the present disclosure, and the advantages thereof, reference is now made to the following descriptions taken in conjunction with the accompanying drawings, wherein like numbers designate like objects, and in which.

DETAILED DESCRIPTION

FIGS. 1 through 4, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged device. The numerous innovative teachings of the present application will be described with reference to exemplary non-limiting embodiments.

Figure 1:
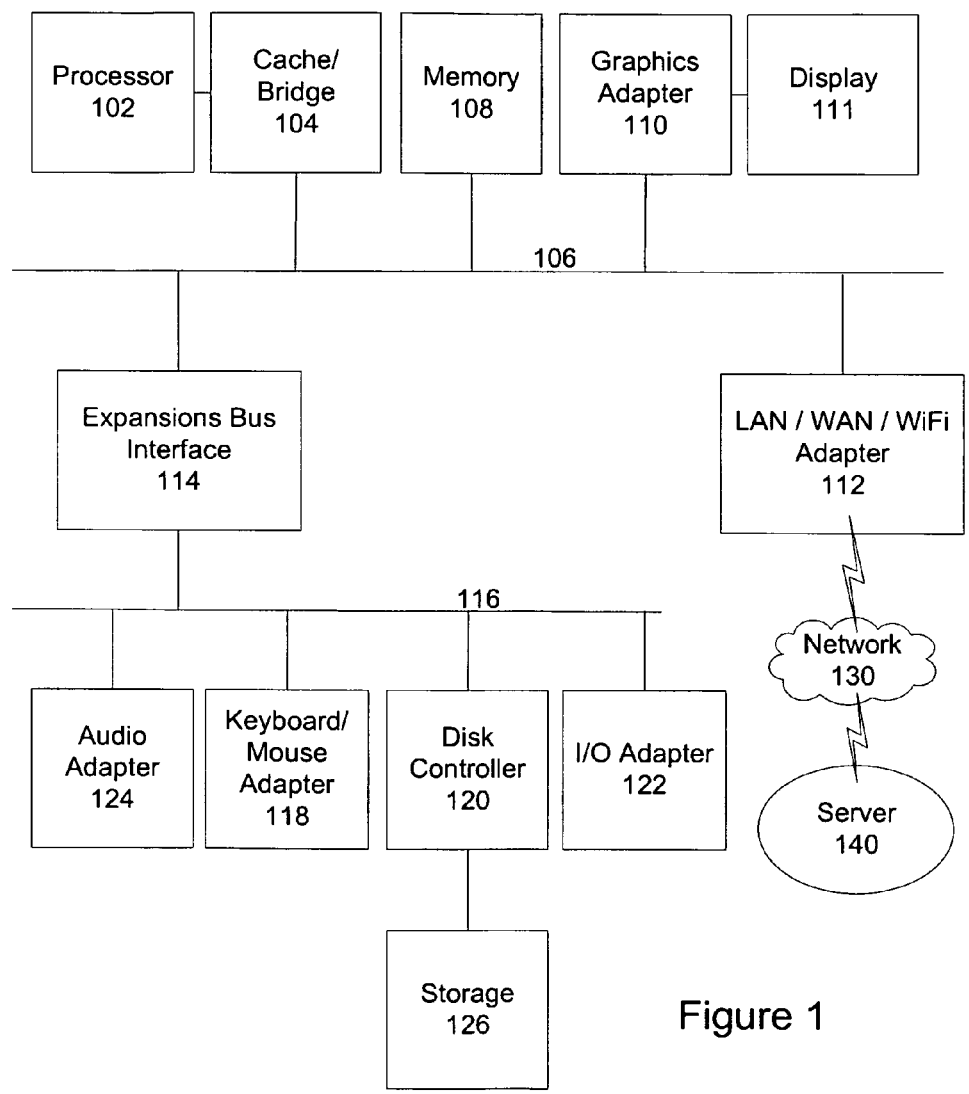
FIG. 1 depicts a block diagram of a data processing system in accordance with a disclosed embodiment.

FIG. 1 depicts a block diagram of a data processing system in accordance with a disclosed embodiment. The data processing system depicted includes a processor 102 connected to a level two cache/bridge 104, which is connected in turn to a local system bus 106. Local system bus 106 may be, for example, a peripheral component interconnect (PCI) architecture bus. Also connected to local system bus in the depicted example are a main memory 108 and a graphics adapter 110. The graphics adapter 110 may be connected to display 111.

Other peripherals, such as local area network (LAN)/Wide Area Network/Wireless (e.g. WiFi) adapter 112, may also be connected to local system bus 106. Expansion bus interface 114 connects local system bus 106 to input/output (I/O) bus 116. I/O bus 116 is connected to keyboard/mouse adapter 118, disk controller 120, and I/O adapter 122. Disk controller 120 can be connected to a storage 126, which can be any suitable machine usable or machine readable storage medium, including but not limited to nonvolatile, hard-coded type mediums such as read only memories (ROMs) or erasable, electrically programmable read only memories (EEPROMs), magnetic tape storage, and user-recordable type mediums such as floppy disks, hard disk drives and compact disk read only memories (CD-ROMs) or digital versatile disks (DVDs), and other known optical, electrical, or magnetic storage devices.

Also connected to I/O bus 116 in the example shown is audio adapter 124, to which speakers (not shown) may be connected for playing sounds. Keyboard/mouse adapter 118 provides a connection for a pointing device (not shown), such as a mouse, trackball, trackpointer, etc.

Those of ordinary skill in the art will appreciate that the hardware depicted in FIG. 1 may vary for particular. For example, other peripheral devices, such as an optical disk drive and the like, also may be used in addition or in place of the hardware depicted. The depicted example is provided for the purpose of explanation only and is not meant to imply architectural limitations with respect to the present disclosure.

A data processing system in accordance with an embodiment of the present disclosure includes an operating system employing a graphical user interface. The operating system permits multiple display windows to be presented in the graphical user interface simultaneously, with each display window providing an interface to a different application or to a different instance of the same application. A cursor in the graphical user interface may be manipulated by a user through the pointing device. The position of the cursor may be changed and/or an event, such as clicking a mouse button, generated to actuate a desired response.

One of various commercial operating systems, such as a version of Microsoft Windows®, a product of Microsoft Corporation located in Redmond, Wash. may be employed if suitably modified. The operating system is modified or created in accordance with the present disclosure as described.

LAN/WAN/Wireless adapter 112 can be connected to a network 130 (not a part of data processing system 100), which can be any public or private data processing system network or combination of networks, as known to those of skill in the art, including the Internet. Data processing system 100 can communicate over network 130 with server system 140, which is also not part of data processing system 100, but can be implemented, for example, as a separate data processing system 100.

In specific embodiments, data processing system 100, using I/O Adapter 122 for example, can send voice telephone messages to subscribers, and/or other communications channels such as email, text, web chat, etc.

Many healthcare businesses have a need to provide prescription refill reminders to consumers and many would like to reduce the cost and/or increase the value of this interaction. A significant percentage of prescriptions are not refilled—leaving a patient susceptible to reduced health outcomes, such as not completing an antibiotic treatment, failing to take blood pressure or cholesterol medication, etc. Health plans and government payers want consumers to stay compliant with their medications to avoid expensive and life threatening complications.

Healthcare providers want to reduce the cost of refill approvals and/or create more value around the interaction, for example to generate clinic and diagnostic revenue through a follow-up appointment, etc.

Pharmacy Benefit Managers want to keep their employer and health plan customers satisfied by helping make consumers more compliant. Retail pharmacy and grocery chains want to capture more prescription refill business and drive more traffic into their stores. Pharmaceutical companies want to ensure consumers continue to use their drugs and would like to have more direct interaction with the consumers of their products.

Disclosed embodiments provide a prescription refill reminder service and system to any company in the heath care system, including Healthcare Providers, Health Plans, Government Payers, Pharmacy Benefit Managers, Drug Store and Grocery Chain Pharmacies, Employers, Pharmaceutical Companies, etc. The disclosed embodiments can proactively send messages in a variety of forms to subscribers on behalf of the company customers.

In some very basic embodiments, the system provides a hosted telecommunications platform and application priced on a per-minute or per-transaction basis. Other embodiments include a system that aggregates content and revenue from the pharmaceutical companies and distributes it through the payers, providers, pharmacy benefit managers (PBMs), pharmacies, and employers who "own" the consumer relationship.

Figure 2:
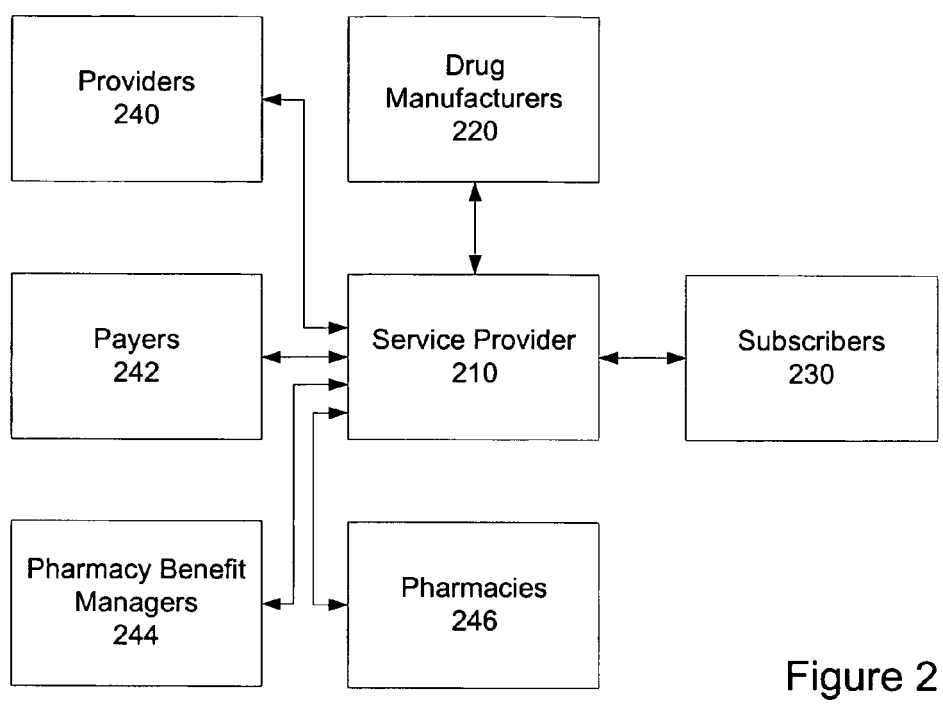
FIG. 2 depicts a high-level block diagram of a system in accordance with a disclosed embodiment.

FIG. 2 depicts a high-level block diagram of a system in accordance with a disclosed embodiment. Here, service provider 210 can be implemented as one or more data processing systems 100, and is configured to perform processes as described herein.

Service provider 210 can send messages to subscribers 230, such as voice telephone messages, email, text, web chat, and others. Typically, these messages are without cost to the subscribers 230, and can include prescription refill reminders, doctor and other appointment reminders, advertisements, recall notices, and other general information that may be useful to the subscribers 230 or that the service provider's customers may wish delivered. These can be delivered via inbound and outbound automated agents.

Figure 3:
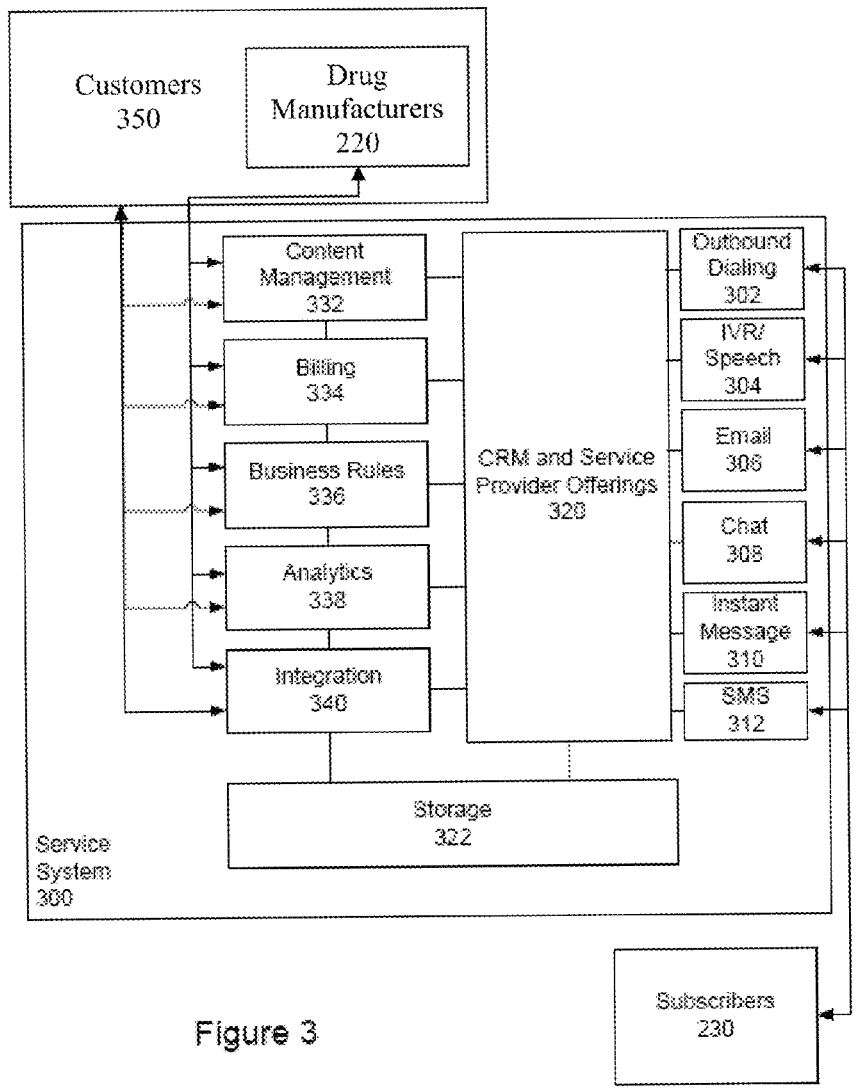
FIG. 3 depicts a block diagram of components of a service system in accordance with a disclosed embodiment.

The customers of service provider 210 can include, for example, providers 240, such as doctors and hospitals, payers 242, such as insurance companies and the government, pharmacy benefit managers (PBMs) 244, and pharmacies 246 (also shown collectively as customers 350 in FIG. 3). Any of these customers may contract with service provider 210 to deliver reminders, informational messages, advertisements, or other messages to subscribers 230. Further, drug manufacturers 220 can also be customers of service provider 210 for the same type of message services.

FIG. 3 depicts a block diagram of components of a service system 300, as can be used by service provider 240, in accordance with a disclosed embodiment. Service system 300 can be implemented, for example, in a data processing system 100 executing a computer program product to perform the processes described herein.

Service system 300 includes a number of functional components, including customer relationship management (CRM) and Service Provider Offerings component 320, which interacts with content management component 332, billing component 334, business rules component 336, analytics component 338, and integration component 340. Each of these components can interact with each other, with storage 322, and with customers 350 and drug manufacturers 220.

CRM and service provider offerings component 320 can perform such functions as generating appropriate content for subscribers 230, interacting with subscribers to provide information and otherwise respond to inquiries, managing communications between subscribers 230 and customers 350, and providing other service provider content offerings to customers 230.

Content management component 332 manages the content supplied by customers 350 and drug manufacturers 220 to be delivers to subscribers 230, including in particular prescription refill reminder content.

Billing component 334 tracks messages and other interactions with subscribers 230 to properly bill one or more of customers 350, drug manufacturers 220, and subscribers 230 for the services.

Business rules component 336 manages interactions between service system 300 and customers 350, drug manufacturers 220, and subscribers 230 according to business rules, and according in particular to the service agreements made between the service provider and customers 350, drug manufacturers 220, and subscribers 230.

Analytics component 338 maintains and analyzes data regarding interactions with subscriber 230 and the data sent and received. The analyzed data is stored and provided to customers for billing and other purposes.

Integration component 340 integrates the various functions of the components to provide an integrated front end and control system for operators, customers 350, and drug manufacturers 220.

Storage 322, which can be implemented as storage 126 and/or memory 108, stores the data received, collected, manipulated, analyzed, and produced by each of the components of service system 300.

CRM and Service Provider Offerings 320 also interacts with subscribers 230 using one or more of outbound dialing component 302, interactive voice response (IVR)—Speech component 304, email component 306, internet chat component 308, instant message component 310, and short message service (SMS) component 312. Dialing component 302 enables service system 300 to dial outbound telephone calls. IVR/speech component 304 enables service system 300 to interact with subscribers 230 using a voice telephone call, with voice prompts and spoken and/or keypress responses. Email component 306 enables service system 300 to interact with subscribers 230 using electronic mail. Internet chat component 308 and instant message (IM) component enable service system 300 to interact with subscribers 230 using a real-time chat and messaging functions over the Internet or other network. SMS component 312 enables service system 300 to interact with subscribers 230 using text messaging functions to, for example, mobile devices. Each of outbound dialing component 302, interactive voice response (IVR)—Speech component 304, email component 306, internet chat component 308, instant message component 310, and short message service (SMS) component 312 can be implemented using conventional products and techniques known to those of skill in the art.

Figure 4:
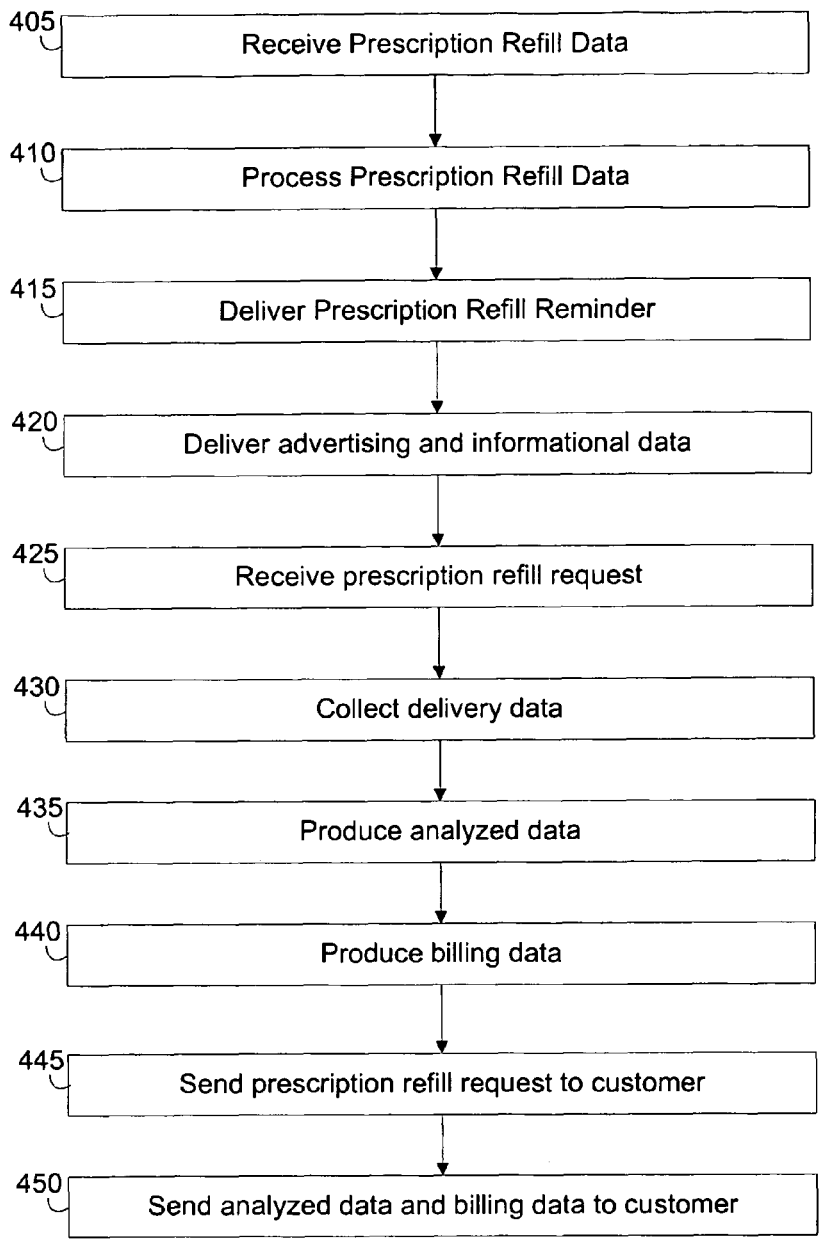
FIG. 4 depicts a flowchart of a process in accordance with various disclosed embodiments.

FIG. 4 depicts a flowchart of a process performed by service system 300, in accordance with various disclosed embodiments.

At step 405, service system 300 receives prescription refill data, advertising and informational data, and other data, from customers 350. This data is typically includes multiple prescriptions for multiple subscribers 230. The prescription refill data is stored in storage 322, At step 410, service system 300 processes the prescription refill data according to business rules used by business rules component 336.

At step 415, service system 300 delivers a prescription refill reminder to a customer 230 according to the prescription refill data and the business rules. This delivery is performed using one or more of outbound dialing component 302, IVR/speech component 304, email component 306, internet chat component 308, instant message component 310, and SMS component 312.

At step 420, service system 300 sends advertising and informational data to a customer 230 according to the business rules and managed by content management system 332. This advertising and informational data can also include data produced by CRM and service provider offerings component 320 by analyzing the prescription refill reminders sent to subscribers 230 and determining appropriate advertising and informational data that corresponds to the prescribed drugs. This delivery is performed using one or more of outbound dialing component 302, IVR/speech component 304, email component 306, internet chat component 308, instant message component 310, and SMS component 312.

At step 425, service system 300 receives a prescription refill request from a subscriber 230. This can occur during the delivery of the refill reminder, advertising data, or informational data.

At step 430, service system 300 collects delivery data corresponding to the delivery of prescription refill reminders, advertising data, and informational data delivered to subscribers 230, and any prescription refill requests received. This can be performed by analytics component 338.

At step 435, service system 300 produces and stores analyzed data according to the collected delivery data. This can be performed by analytics component 338.

At step 440, service system 300 produces billing data according to the analyzed data. This can be performed by billing component 334.

At step 445, any prescription refill requests are both stored and sent to the appropriate customer 250 to be filled. The prescription refill request will include at least an identifier of the prescription to be refilled and the subscriber 230 refilling the prescription.

At step 450, analyzed data and billing data is both stored and sent to customers 350. This can be performed by billing component 334. Customers then pay for the reminders, advertising data, and informational data delivered to subscribers 230.

Disclosed embodiments provide significant advantages over known system. For example, using a service system 300 as disclosed herein, consumers can better manage their health by staying compliant with their medication regimens and are no longer required to remember to visit or call their pharmacy provider to request refills or their doctor to have prescriptions renewed. Pharmacies and Pharmacy Benefit Managers will benefit by making their services more convenient and valuable to consumers, payers, and employers. Physicians will benefit from the improved medical outcomes of their patients and will have new mechanisms to deliver important healthcare information between patient visits. Drug manufacturers will benefit from greater consumer compliance with drug usage guidelines and will have a communications channel to provide consumers with information to optimize their medical outcomes and better manage their health. Healthcare companies are no longer required to provide staff to handle calls or set up systems to handle communications with consumers.

Various systems as disclosed herein use proactive communications with subscribers 230 including multi-channel communications such as an agent, IVR, automated outbound call, e-mail, etc.

Various embodiments also include a platform or "exchange" for aggregating and distributing prescription related content that all companies in the healthcare ecosystem, including customers 350 and drug manufacturers 220, can plug into. Various embodiments also include aggregating content and revenue from the customers 350 and drug manufacturers 220 that can be distributed through the exchange to parties that "own" the consumer relationship. Various embodiments also include providing services which protect the security and privacy of subscribers and prevent the undesired disclosure of one company's customers to another.

Various embodiments also include providing related value added services, e.g., providing additional information, collecting additional information, making up-sell and cross-sell offers, performing transaction processing, conducting commerce, etc., in addition to the basic reminder.

Those skilled in the art will recognize that, for simplicity and clarity, the full structure and operation of all data processing systems suitable for use with the present disclosure is not being depicted or described herein. Instead, only so much of a data processing system as is unique to the present disclosure or necessary for an understanding of the present disclosure is depicted and described. The remainder of the construction and operation of data processing system 100 may conform to any of the various current implementations and practices known in the art.

It is important to note that while the disclosure includes a description in the context of a fully functional system, those skilled in the art will appreciate that at least portions of the mechanism of the present disclosure are capable of being distributed in the form of a instructions contained within a machine usable medium in any of a variety of forms, and that the present disclosure applies equally regardless of the particular type of instruction or signal bearing medium utilized to actually carry out the distribution. Examples of machine usable or machine readable mediums include: nonvolatile, hard-coded type mediums such as read only memories (ROMs) or erasable, electrically programmable read only memories (EEPROMs), and user-recordable type mediums such as floppy disks, hard disk drives and compact disk read only memories (CD-ROMs) or digital versatile disks (DVDs).

Although an exemplary embodiment of the present disclosure has been described in detail, those skilled in the art will understand that various changes, substitutions, variations, and improvements disclosed herein may be made without departing from the spirit and scope of the disclosure in its broadest form.

None of the description in the present application should be read as implying that any particular element, step, or function is an essential element which must be included in the claim scope: the scope of patented subject matter is defined only by the allowed claims. Moreover, none of these claims are intended to invoke paragraph six of 35 USC §112 unless the exact words "means for" are followed by a participle.

What is claimed is:

1. A data processing system comprising:
    a processor;
    memory coupled to the processor,
    the processor to receive, from a plurality of customers, prescription refill data;
    the processor to process the prescription refill data according to business rules;
    the processor to aggregate advertising from drug manufacturers;
    the processor to determine advertising, from among the aggregated advertising, that corresponds to the prescription refill data;
    the processor to send, to a subscriber, a prescription refill reminder according to the prescription refill data and the business rules;
    the processor to send, to the subscriber, the determined advertising and informational data corresponding to the prescription refill reminder;
    the processor to receive, from the subscriber, a prescription refill request based on the prescription refill reminder; and
    the processor to electronically transmit, to one of the plurality of customers, the prescription refill request based on the prescription refill data,
    the customers comprising at least one entity selected from the group consisting of drug manufacturers, providers, payers, and pharmacy benefit managers,
    the subscriber different from any of the customers.

2. The data processing system of claim 1, the processor to send, to the subscriber, informational data corresponding to the prescription refill reminder.

3. The data processing system of claim 1, the processor to collect delivery data according to the prescription refill reminder, the determined advertising, and informational data.

4. The data processing system of claim 3, the processor to analyze the delivery data to produce analyzed data.

5. The data processing system of claim 4, the processor to send the analyzed data to at least one of the plurality of customers.

6. The data processing system of claim 1, the processor to produce billing data according to the prescription refill reminder, the determined advertising, and informational data.

7. The data processing system of claim 1, the processor to send, to the subscriber, at least one of additional information, up-sell offers, and cross-sell offers.

* * * * *